United States Patent
Srinivasan et al.

(10) Patent No.: US 7,232,905 B2
(45) Date of Patent: Jun. 19, 2007

(54) SUBSTITUTED DIHYDROPYRIMIDINONE PREPARATION USING POLYANILINE SALT CATALYST

(75) Inventors: Palaniappan Srinivasan, Hyderabad (IN); Vaidya J. Rao, Hyderabad (IN); Gangadasu Banda, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 309 days.

(21) Appl. No.: 10/810,343

(22) Filed: Mar. 26, 2004

(65) Prior Publication Data

US 2005/0215790 A1    Sep. 29, 2005

(51) Int. Cl.
*C07D 239/02* (2006.01)
*C07D 239/34* (2006.01)

(52) U.S. Cl. ..................... 544/315; 544/318
(58) Field of Classification Search ............. 544/315, 544/318
See application file for complete search history.

(56) References Cited

OTHER PUBLICATIONS

Peter Wipf and April Cunningham, "A solid phase protocol of the biginelli dihydropyrimidine synthesis suitable for combinatorial chemistry", Tetrahedron Letters, vol. 36, No. 43, pp. 7819-7822, 1995.

*Primary Examiner*—Deepak Rao
(74) *Attorney, Agent, or Firm*—Darby & Darby

(57) ABSTRACT

The present invention provides a process for the preparation of substituted dihydropyrimidinones using polyaniline salts as reusable catalysts, which comprises reacting an aldehyde, a β-keto ester and urea/thiourea in the presence of a polyaniline salt catalyst and separating the substituted dihydropyrimidinone obtained.

10 Claims, No Drawings

SUBSTITUTED DIHYDROPYRIMIDINONE PREPARATION USING POLYANILINE SALT CATALYST

FIELD OF THE INVENTION

The present invention relates to a process for the preparation of substituted dihydropyrimidinones using polyaniline salts as catalysts.

BACKGROUND OF THE INVENTION

Substituted dihydropyrimidinone compounds has excellent activity against the viruses of the trachoma group. Some of the analogs of Dihydropyrimidine compounds are antitumour agents and formed to be active against Walker carcinosarcoma in rats and mice. The cardiovascular activity of Biginelli compounds, namely of β-amino ethyl ester was first discovered by Khanina and co-workers in 1978. Since 1986 the number of publications and patents dealing with the cardiovascular activity of dihydropyrimidine has grown rapidly.

Dihydropyrimidinones have emerged as the integral backbones of calcium channel blockers (a. Rovnyak, G. C et al, J. Med. Chem., 1995, vol 38, p-119–129; b. Atwal, K. S et al J. Med. Chem., 1990, vol 33, p-2629–2635), antihypertensive agents (Atwal, K. S et al, J. Med. Chem., 1991, vol 34, p-806–811), α-adrenergic and neuropeptide Y (NPY) antagonists.

Several marine alkaloids containing the dihydropyrimidine core unit have shown interesting biological properties (a. Overman L. E et al J. Am. Chem. Soc., 1995, vol 117, p-2657–2658; b. Snider, B. B et al J. Org. Chem., 1993, vol 58, p-3828–3839). Batzelladine alkaloids have been found to be potent HIV gp-120-CD4 inhibitors (a. Snider, B. B et al Tetrahedron Lett., 1996, vol 37, p-6977–6980; b. Patil, A. D et al J. Org. Chem., 1995, vol 60, p-1182–1188). In addition, these compounds exhibit a broad range of biological activities. (Kappe, C. O Tetrahedron, 1993, vol 49, p-6937–6963.) such as antiviral, antitumor, antibacterial and anti-inflammatory properties.

Dihydropyrimidinone compounds show a diverse range of biological activity. In recent years, however, interest in these compounds has increased rapidly, and the scope of the original cyclocondensation reaction has been widely extended by variation of all the compounds and conditions. The present popularity of these compounds is mainly due to their close structural relationship to the clinically important dihydropyrimidine calcium channel blockers of the nifedipine-type.

In 1893 Pietro Biginelli reported the first synthesis of 3,4-dihydropyrimidin-2(1H)-ones of compounds by a very simple one-pot condensation reaction of an aromatic aldehyde, urea and ethyl acetoacetate in ethanolic solution. Hence this type of compounds denoted as Biginelli compounds. However, the main draw back of Biginille reaction is unsatisfactory yields obtained in the case of substituted aromatic and aliphatic aldehydes (a. Wipf, P et al Tetrahedron Lett., 1995, vol 36, p-7819–7822; b. Folkers, K et al J. Am. Chem. Soc., vol 56, 1934, p-1180–1185). This has led to the disclosure of multi-step strategies (O Reilly, B. C et al Heterocycles 1987, vol 26, p-1185–1188.) that produce somewhat higher yields but lack the simplicity of the original Biginelli one-pot synthesis. At present several improved procedures have been reported such as Lewis Acids (a. ZrCl$_4$: Reddy, Ch. V. et al Tetrahedron. Lett., 2002, vol 43, p-2657–2659; b. InBr$_3$: Fu, N. Y. et al Tetrahedron 2002, vol 58, p-4801–4807; c. BiCl$_3$: Rama Linga, K et al Synlett 2001, No. 6, p-863–865; d. LiClO$_4$: Yadav. J. S et al Synthesis 2001, p-1341–1345; e. BF$_3$-0Et$_2$: Hu, E. H et al J. Org. Chem. 1998, vol 63, p-3454–3457), Triflates (a. La (OTf)$_3$: Ma, Y et al J. Org. Chem., 2000, vol 65, p-3864–3868; b. Bi (OTf)$_3$: Adapa, S. R et al Synlett 2002, p-67; c) Cu (OTf)$_2$: Paraskar, A. S et al Tetrahedron Lett. 2003, vol 44, p-3305–3308.) and soluble polymer supported liquid phase synthesis (Xia, M et al Tetrahedron Lett. 2002, vol 43, p-7703–7705). However in spite of their potential utility, many of these methods involve expensive reagents, strongly acidic conditions, longer reaction times, and unsatisfactory yields. In recent years the development of more economical and environmental friendly conversion process is gaining interest in the chemical community.

OBJECTS OF THE INVENTION

The main object of the present invention is to provide a process for the preparation of substituted dihydropyrimidinones using polyaniline salts as catalysts, which obviates the drawbacks detailed above.

SUMMARY OF THE INVENTION

Accordingly, the present invention provides a process for the preparation of substituted dihydropyrimidinones using polyaniline salts as reusable catalysts, which comprises reacting an aldehyde, a β-keto ester and urea/thiourea in the presence of a polyaniline salt catalyst and separating the dihydropyrimidine obtained thereby.

In another embodiment of the invention, the aldehyde is selected from the group consisting of Benzaldehyde, 4-Methoxybenzaldehyde, 4-Chlorobenzaldehyde, 4-Hydroxybenzaldehyde, 4-Methyl benzaldehyde, 4-(Dimethylamino) benzaldehyde, 4-Nitrobenzaldehyde, 4-(Phenoxy) benzaldehyde, β-Naphthal, Cinnamaldehyde, Furfuraldehyde and Heptaldehyde.

In another embodiment of the invention, the β-keto ester is selected from the group consisting of methyl acetoacetate and ethyl acetoacetate.

In another embodiment of the invention, the substrate used is selected from urea and thiourea.

In yet another embodiment of the invention, the polyaniline salt catalyst is selected from the group consisting of polyaniline-sulfate, polyaniline-hydrochloride, polyaniline-perchlorate, polyaniline-phosphate, polyaniline-nitrate, polyaniline-aluminum chloride, polyaniline-ferric chloride, polyaniline-bismuth chloride, polyaniline-p-toluene sulfonate, and polyaniline-sulfosalicylate system.

In another embodiment of the invention, the reaction is carried out at a temperature in the range of 25 to 65° C.

In another embodiment of the invention, the reaction is carried out for a period of 2 to 6 hrs.

In yet another embodiment of the present invention, the catalyst is used in an amount of 1 to 10 wt % with respect to aldehyde.

In another embodiment of the present invention, the reaction is carried out in the presence of a solvent selected from the group consisting of methanol, ethanol, acetonitrile and tetrahydrofuran.

In another embodiment of the invention, the substituted dihydropyrimidinones are separated by filtration.

In another embodiment of the invention, the catalyst is recycled.

DETAILED DESCRIPTION OF THE INVENTION

The present invention provides a process for the preparation of substituted dihydropyrimidinones using polyaniline salts as reusable catalysts. The process essentially comprises reacting a reaction mixture comprising an aldehyde, a β-keto ester and urea/thiourea substrate in the presence of a polyaniline salt catalyst and separating the substituted dihydropyrimidinone obtained thereby.

The aldehyde can be Benzaldehyde, 4-Methoxybenzaldehyde, 4-Chlorobenzaldehyde, 4-Hydroxybenzaldehyde, 4-Methyl benzaldehyde, 4-(Dimethylamino) benzaldehyde, 4-Nitrobenzaldehyde, 4-(Phenoxy) benzaldehyde, P-Naphthal, Cinnamaldehyde, Furfuraldehyde or Heptaldehyde. The β-keto ester can be methyl acetoacetate or ethyl acetoacetate. Reaction is carried out in presence of a substrate which can be urea or thiourea.

The polyaniline salt used as a catalyst is selected from polyaniline-sulfate, polyaniline-hydrochloride, polyaniline-perchlorate, polyaniline-phosphate, polyaniline-nitrate, polyaniline-aluminum chloride, polyaniline-ferric chloride, polyaniline-bismuth chloride, polyaniline-p-toluene sulfonate, and polyaniline-sulfosalicylate system. Preparation of the catalyst is given in detail in Example 1.

The reaction is preferably carried out at a temperature in the range of 25 to 65° C. and for a time period in the range of 2 to 6 hrs.

The catalyst is used in an amount of 1 to 10 wt % with respect to aldehyde and the reaction is preferably carried out in the presence of a solvent selected from the group consisting of methanol, ethanol, acetonitrile and tetrahydrofuran. The substituted dihydropyrimidinones can be isolated such as filtration followed by isolation of product by conventional methods. A significant advantage of the present invention is that the catalyst can be recycled to reaction mixture without significant loss in activity.

The novelty of the invention lies in the use of polyaniline-salts as catalysts in the preparation of substituted dihydropyrimidinones for the first time. Also, the use of polyaniline salts as catalysts provides the following advantages (i) separation of catalyst from a reaction mixture is easy, (ii) repeated use of catalyst is possible, (iii) there is no problem for the disposal of used catalyst as they are environmentally safe, (iv) the preparation of the catalyst is straight forward synthetic route and (v) various polyaniline salts can be used.

The following examples are given by way of illustration and therefore should not be construed as limiting the scope of the present invention.

EXAMPLE 1

Preparation of Polyaniline Salts 10 ml of aniline was added to the 700 ml aqueous solution containing 30 ml $H_2SO_4$ taken in 2 lits round bottomed flask. The solution was kept under constant stirring at 5–10° C. To this solution, 23.8 g of sodium per sulfate in 250 ml of water was added drop wise for 30 minutes. The reaction was allowed to continue for 4 hrs. The precipitated polyaniline-sulfate salt was recovered by filtration, and the precipitate was washed with 2 liters of distilled water followed by 500 ml acetone. Thus obtained polyaniline sulfate salt was dispersed in 1000 ml sodium hydroxide solution (1N) and stirred for 12 hrs at ambient temperature. The solution was filtered, washed several times with water to remove excess NaOH. Product (polyaniline base) was dried at 100° C. for 12 hrs until constant mass was reached.

Polyaniline salts such as polyaniline-sulfate, polyaniline-hydrochloride polyaniline-perchlorate, polyaniline-nitrate, polyaniline-phosphate were prepared by following procedure:

Polyaniline base (1 g) prepared by the above method was added to 100 ml aqueous solution containing 1 M of acid ($H_2SO_4$/HCl/$HClO_4$/$HNO_3$/$H_3PO_4$). The solution was kept under stirring for 4 hrs at ambient temperature. The solution was filtered, washed with 500 ml water followed by 100 ml acetone. The powder was dried at 100° C. till a constant mass.

Polyaniline salts such as polyaniline-aluminium chloride, polyaniline-ferric chloride, polyaniline-bismuth chloride, polyaniline-p-toulene sulfonate, polyaniline-سulfosalicylate were prepared by the following procedure:

Polyaniline base (1 g) prepared by the above method was added to 100 ml acetone containing 1 M of acid ($AlCl_3$/$FeCl_3$/$BiCl_3$/p-toulene sulfonic acid/sulfosalicylic acid). The solution was kept under stirring for 4 hrs at ambient temperature. The solution was filtered, washed with 100 ml acetone. The powder was dried at 100° C. till a constant mass.

EXAMPLE 2

Preparation of Substituted Dihydropyrimidinones Using Different Reaction Times

Benzaldehyde (11.0 g, 9.43 mmol), methyl acetoacetate (1.09 g, 9.43 mmol) and urea (0.56 g. 9.43 mmol) was taken in 25 ml round bottomed flask, 10 ml of methanol was added followed by 50 mg of polyaniline-p-toluene sulfonate salt powder (5 wt % with respect to aldehyde) prepared using example 1. The reaction mixture was refluxed for different intervals of time.

The reaction mixture was filtered at hot condition using Whatman 41 filter paper, methanol solvent was evaporated under vacuum. The crude product obtained was washed with water, filtered and dried at 100° C. The product was purified by recrystalisation using methanol. The precipitated product was filtered and dried at 50° C. till a constant mass. The product was characterized by $^1H$ NMR, EI Mass and IR spectrum. The yield of the product is given in Table I.

TABLE I

| REACTION TIME (minutes) | YIELD (%) |
| --- | --- |
| 30 | 42 |
| 60 | 62 |
| 90 | 82 |
| 120 | 97 |

EXAMPLE 3

Preparation of Substituted Dihydropyrimidinones Using Different Amounts of Catalyst Benzaldehyde (1.0 g, 9.43 mmol), methyl acetoacetate (1.09 g, 9.43 mmol) and urea (0.56 g. 9.43 mmol) was taken in 25 ml round bottomed flask, 10 ml of methanol was added followed by different amounts of polyaniline-p-toluene sulfonate salt powder prepared using example 1. Reaction mixture was refluxed for 2 hrs. Isolation and purification of the product was carried out as reported in example 2. The yield of the product is given in Table II.

TABLE II

| AMOUNT OF THE CATALYST (wt %) | YIELD (%) |
|---|---|
| 1.0 | 22 |
| 2.5 | 36 |
| 5.0 | 97 |
| 7.5 | 97 |
| 10 | 97 |

EXAMPLE 4

Preparation of Substituted Dihydropyrimidinones at Different Temperatures

Benzaldehyde (1.0 g, 9.43 mmol), methyl acetoacetate (1.09 g, 9.43 mmol) and urea (0.56 g. 9.43 mmol) was taken in 25 ml round bottomed flask, 10 ml of methanol was added followed by 50 mg of polyaniline-p-toluene sulfonate salt powder (5 wt % with respect to aldehyde) prepared using example 1. The reaction was carried out at different temperature and for a particular period of time. Isolation and purification of the product was carried out as reported in example 2. The yield of the product is given in Table III.

TABLE III

| TEMPERATURE (° C.) | TIME (hr.) | YIELD (%) |
|---|---|---|
| RT | 16 | Nil |
| 40 | 12 | Nil |
| 50 | 6 | 28 |
| 64 | 2 | 97 |

EXAMPLE 5

Preparation of Substituted Dihydropyrimidinones Using Recovered Catalyst for Six More Times Benzaldehyde (1.0 g, 9.43 mmol), methyl acetoacetate (1.09 g, 9.43 mmol) and urea (0.56 g. 9.43 mmol) was taken in 25 ml round bottomed flask, 10 ml of methanol was added followed by 50 mg of polyaniline-p-toluene sulfonate salt powder (5 wt % with respect to aldehyde) prepared using example 1. Reaction mixture was refluxed for 2 hrs. Isolation and purification of the product was carried out as in example 2. The experiment was carried out for six times more using the recovered catalyst. The yield of the product is given in Table IV.

TABLE IV

| REUSABILITY (Number of Times) | YIELD (%) |
|---|---|
| First | 97 |
| Second | 96 |
| Third | 96 |
| Forth | 97 |
| Fifth | 95 |
| Sixth | 94 |
| Seventh | 96 |

EXAMPLE 6

Preparation of Substituted Dihydropyrimidinones Using Different Polyaniline Salts Benzaldehyde (1.0 g, 9.43 mmol), methyl acetoacetate (1.09 g, 9.43 mmol) and urea (0.56 g. 9.43 mmol) was taken in 25 ml round bottomed flask, 10 ml of methanol was added followed by various types of polyaniline-salts (5–10 wt % with respect to aldehyde) prepared using example 1. The reaction mixture was refluxed for 2 to 4 hrs. Isolation and purification of the product was carried out as reported in example 2. The amount of the catalyst, time, yield and reusability of the catalyst are given in Table V.

TABLE V

| CATALYST | CATALYST AMOUNT (wt %) | TIME (hrs) | YIELD (%) | REUSABILITY CHECKED (No. of times) |
|---|---|---|---|---|
| Polyaniline-sulfate | 10 | 3 | 95 | 4 |
| Polyaniline-hydrochloride | 10 | 4 | 93 | 3 |
| Polyaniline-perchlorate | 10 | 3 | 94 | 3 |
| Polyaniline-nitrate | 10 | 4 | 94 | 3 |
| Polyaniline-phosphate | 10 | 4 | 92 | 3 |
| Polyaniline-aluminium chloride | 5 | 2 | 97 | 4 |
| Polyaniline-ferric chloride | 5 | 2 | 89 | 3 |
| Polyaniline-bismuth chloride | 5 | 2 | 94 | 4 |
| Polyaniline-p-toluene sulfonate | 5 | 2 | 97 | 7 |
| Polyaniline-sulfosalicylate | 10 | 3 | 94 | 3 |

EXAMPLE 7

Preparation of Substituted Dihydropyrimidinones Using Different Solvents

Benzaldehyde (1.0 g, 9.43 mmol), methyl acetoacetate (1.09 g, 9.43 mmol) and urea (0.56 g. 9.43 mmol) was taken in 25 ml round bottomed flask, 10 ml of solvent was added followed by 50 mg of polyaniline-p-toluene sulfonate salt powder (5 wt % with respect to aldehyde) prepared using example 1. The reaction mixture was refluxed for a particular period of time. Isolation and purification of the product was carried out as reported in example 2. The time and yield of the product are given in Table VI.

TABLE VI

| SOLVENTS | TIME (hrs) | YIELD (%) |
| --- | --- | --- |
| Methanol | 2 | 97 |
| Acetonitrile | 2 | 94 |
| Tetrahydrofuran | 2 | 86 |
| Diethyl ether | 12 | Nil |

EXAMPLE 8

Preparation of Different Substituted Dihydropyrimidinones

In an experiment, aldehyde, keto ester and urea/thiourea was taken as one equivalent in round bottomed flask, alcohol was added followed by 5 wt % of polyaniline-bismuth trichloride powder prepared using example 1. The reaction mixture was refluxed for 2 to 6 hrs. Isolation and purification of the product was carried out as reported in example 2. The time and yield of the product are given in Table VII.

TABLE VII

| Substrates | | | Time (hrs) | Yield (%) |
| --- | --- | --- | --- | --- |
| Benzaldehyde | Methyl acetoacetate | Urea | 2 | 94 |
| 4-Methoxybenzaldehyde | Methyl acetoacetate | Urea | 2 | 98 |
| 4-Chlorobenzaldehyde | Methyl acetoacetate | Urea | 5 | 88 |
| 4-Hydroxybenzaldehyde | Methyl acetoacetate | Urea | 5 | 92 |
| 4-Methylbenzaldehyde | Methyl acetoacetate | Urea | 4 | 96 |
| 4-(Dimethylamino) benzaldehye | Methyl acetoacetate | Urea | 6 | 93 |
| 4-Nitrobenzaldehyde | Methyl acetoacetate | Urea | 6 | 93 |
| 4-(phenoxy) benzaldehyde | Methyl acetoacetate | Urea | 4 | 96 |
| β-Naphthal | Methyl acetoacetate | Urea | 5 | 88 |
| Cinnamaldehyde | Methyl acetoacetate | Urea | 4 | 98 |
| Furfuraldehyde | Methyl acetoacetate | Urea | 4 | 85 |
| Heptaldehyde | Methyl acetoacetate | Urea | 4 | 86 |
| 4-Methoxybenzaldehyde | Methyl acetoacetate | Thiourea | 4 | 85 |
| 4-Hydroxybenzaldehyde | Methyl acetoacetate | Thiourea | 6 | 82 |
| 4-Methoxybenzaldehyde | Ethyl acetoacetate | Thiourea | 4 | 84 |
| 4-Nitrobenzaldehyde | Ethyl acetoacetate | Urea | 6 | 82 |

Advantages of the invention

The main advantages of the present invention are: the use of polyaniline-salts as catalyst in the preparation of substituted dihydropyrimidinones for the first time. Also, the use of polyaniline salts as catalysts provides the following advantages (i) separation of catalyst from a reaction mixture is easy, (ii) repeated use of catalyst is possible, (iii) there is no problem for the disposal of used catalyst as they are environmentally safe, though the disposal of mineral acid catalyst requires much money for treatment to make it environmentally safe, (iv) the preparation of the catalyst is straight forward synthetic route and (v) various polyaniline salts can be used.

In view of the above, it will be seen that several advantages of the invention are achieved and other advantageous results attained. As various changes could be made in the above methods and compositions without departing from the scope of the invention, it is intended that all matter contained in the above description shall be interpreted as illustrative and not in a limiting sense.

We claim:

1. A process for the preparation of a substituted dihydropyrimidinone using a polyaniline salt as a reusable catalyst, which comprises reacting an aldehyde, a β-keto ester and urea or thiourea in the presence of a polyaniline salt catalyst and separating the substituted dihydropyrimidinone obtained thereby.

2. The process as claimed in claim 1 wherein the aldehyde is selected from the group consisting of Benzaldehyde, 4-Methoxybenzaldehyde, 4-Chlorobenzaldehyde, 4-Hydroxybenzaldehyde, 4-Methyl benzaldehyde, 4-(Dimethylamino) benzaldehyde, 4-Nitrobenzaldehyde, 4-(Phenoxy) benzaldehyde, β-Naphthal, Cinnamaldehyde, Furfuraldehyde and Heptaldehyde.

3. The process as claimed in claim 1 wherein the β-keto ester is selected from the group consisting of methyl acetoacetate and ethyl acetoacetate.

4. The process as claimed in claim 1 wherein the polyaniline salt catalyst is selected from the group consisting of polyaniline-sulfate, polyaniline-hydrochloride, polyaniline-perchlorate, polyaniline-phosphate, polyaniline-nitrate, polyaniline-aluminum chloride, polyaniline-ferric chloride, polyaniline-bismuth chloride, polyaniline-p-toluene sulfonate, and polyaniline-sulfosalicylate system.

5. The process as claimed in claim 1 wherein the reaction is carried out at a temperature in the range of from 25° C. to 65° C.

6. The process as claimed in claim 1 wherein the reaction is carried out for a period of from 2 hours to 6 hours.

7. The process as claimed in claim 1 wherein the catalyst is used in an amount of from 1 to 10 weight percent with respect to the aldehyde.

8. The process as claimed in claim 1 wherein the reaction is carried out in the presence of a solvent selected from the group consisting of methanol, ethanol, acetonitrile and tetrahydrofuran.

9. The process as claimed in claim 1 wherein the substituted dihydropyrimidinone is separated by filtration.

10. The process as claimed in claim 1 wherein the catalyst is recycled.

* * * * *